United States Patent
Yong

Patent Number: 5,728,043
Date of Patent: Mar. 17, 1998

[54] SIMPLIFIED ERECTION AID DEVICE

[76] Inventor: Joseph C. Yong, 3108 W. Hammer La., Stockton, Calif. 95209

[21] Appl. No.: 545,420

[22] Filed: Oct. 19, 1995

[51] Int. Cl.⁶ .................................................. A61F 5/00
[52] U.S. Cl. ................................................ 600/39; 600/39
[58] Field of Search ........................................ 600/38–41

[56] References Cited

U.S. PATENT DOCUMENTS

| | | | |
|---|---|---|---|
| 1,511,572 | 10/1924 | Marshall | 600/39 |
| 4,381,000 | 4/1983 | Duncan | 600/39 |
| 4,429,689 | 2/1984 | Yanong | 600/39 |
| 4,488,541 | 12/1984 | Garcia | 600/39 |
| 5,244,454 | 9/1993 | Coates | 600/41 |

*Primary Examiner*—Jennifer Bahr
*Assistant Examiner*—Samuel Gilbert

[57] ABSTRACT

An erection aid device, comprising a disk that defines an opening slightly smaller than a user's fully erect penis, a set of connecting straps and a rigid extension arm that is fixed to the disk, with the extension arm shaped so that it can be attached to a belt worn around the user, while holding the disk in a vertical position against the base of the penis. The user pushes their penis through the opening in the disk, and slides the disk to the base of the penis. The scrotum is positioned between two connecting lines, that are connected to a belt on one end, and the disk on the other end. The connecting lines pull the disk, so that it presses against the user's groin area, with the rigid extension arm maintaining the disk in a vertical position. The pressure of the disk against the user's body assists in compressing inner vein diameters that drain the corpus cavernosa, without interfering with other normal body functions.

3 Claims, 4 Drawing Sheets

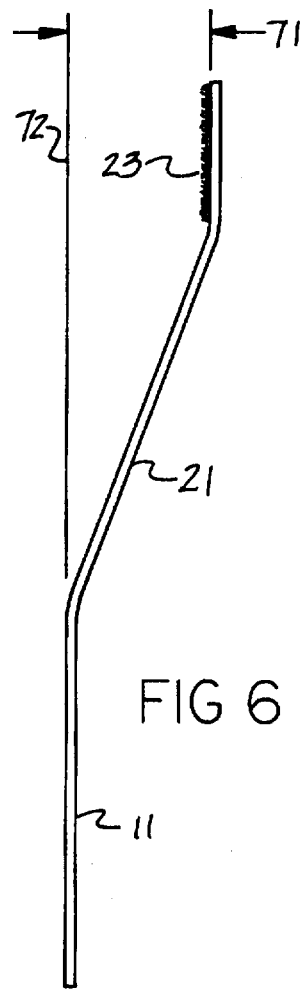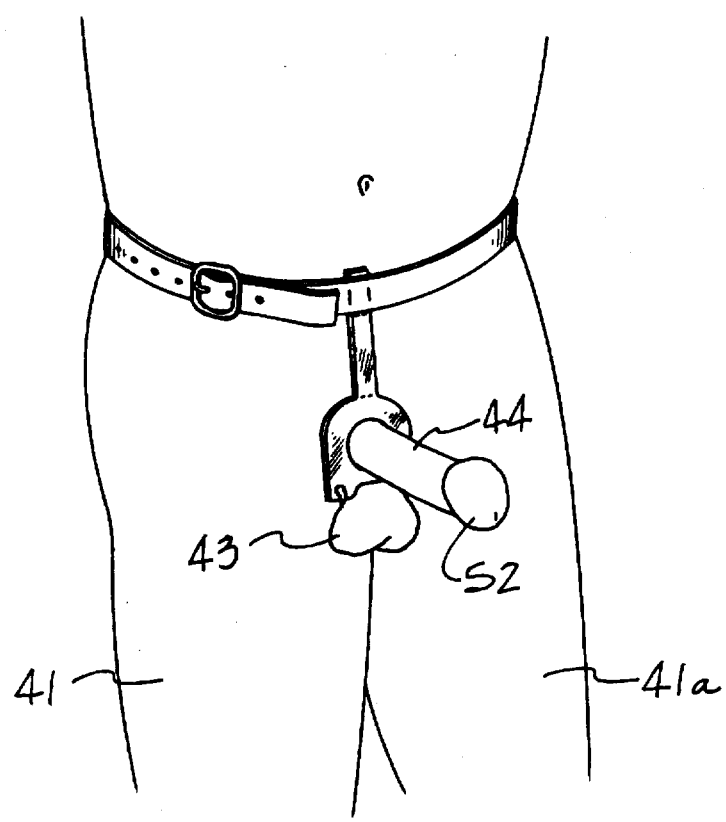
FIG 6
FIG 3

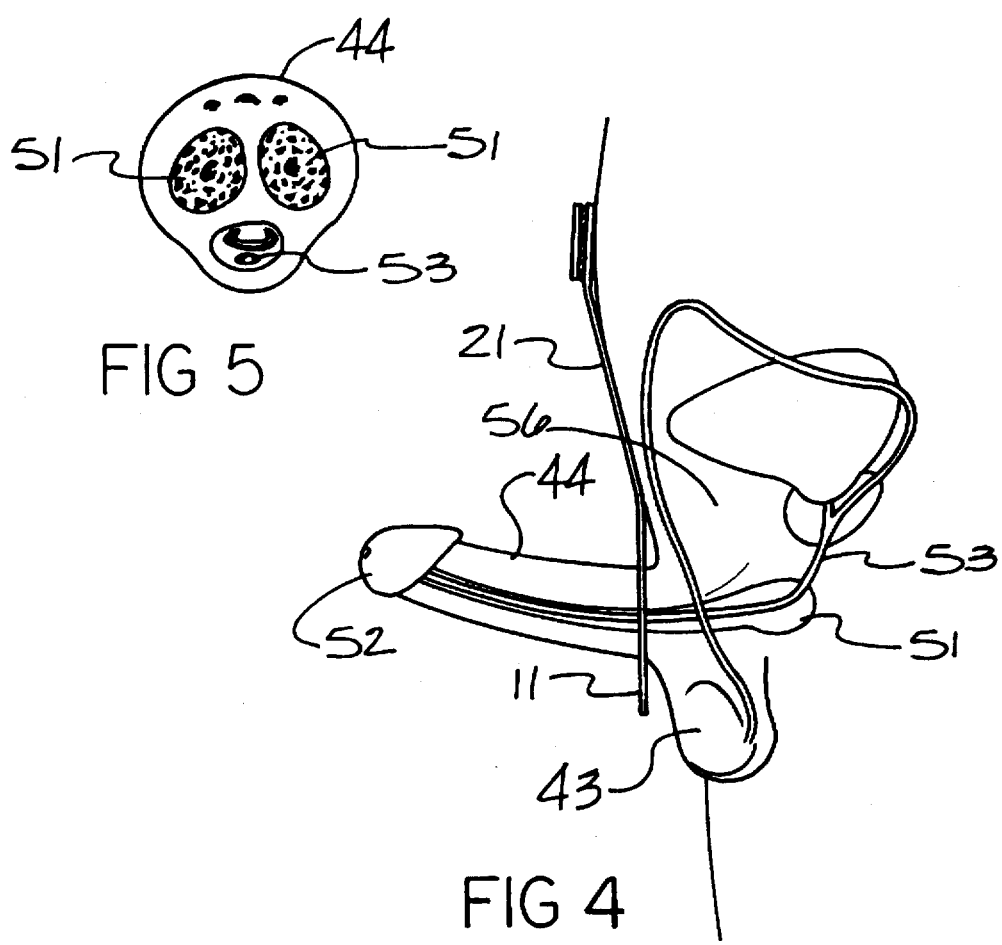

SIMPLIFIED ERECTION AID DEVICE

BACKGROUND OF THE INVENTION

Many human males suffer from impotence, due to their inability to maintain an erection sufficient to engage in desired sexual activity. Numerous approaches have been developed to solve this problem, including, by way of example, prescription drugs, hormone medication, external vacuum therapy, penile injection therapy, penile implants, vascular reconstructive surgery, and sexual counseling and therapy.

The erectile portions of a penis comprise two spongy corpus cavernosum regions, that when filled with blood, expand in size and length. A penis achieves an erection when the male is stimulated sexually, so that a neurotransmitter is released, causing the main artery that delivers blood to the corpus cavernosum to dilate. As more blood is delivered to the corpus cavernosum, it increases in size and length. The expansion eventually compresses the veins that drain blood from these regions, allowing an erection to be maintained.

Impotence occurs when the artery is not sufficiently dilated, or the leakage of the blood from the corpus cavernosum region is too great to create or sustain an erection. Correction of the problem can be psychological, or it can be a physical problem, or a combination of both.

In situations where a male has a physical condition that causes his impotence, sometimes physical mechanisms, as opposed to chemical treatments or therapy, are the only means available to correct the impotence problem. Prior inventions, directed toward correcting impotence, have often given cause for objections to their use. For example, the mechanism involved can be difficult to conceal, interfere with the ability of the user and the partner to fully enjoy sexual activity, or interfere with the normal functions of the penis, urethra, and surrounding tissues.

Devices that are worn around the penis, generally rely on the compression of the penile shaft, so that the blood leakage through the veins that empty the corpus cavernosum region are physically restricted. The restriction is generally spread over an area of the penile shaft, using a tube with a length of 0.5 inches or more, whose inner side contacts a length of the penile shaft. The compression of the penile shaft causes blood flow to be restricted, not only from the corpus cavernosum region, but also affects the rest of the penis, such as the glans.

Devices that rely on the compression of the penile shaft can also interfere with normal bodily functions, such as ejaculation and urination. At least one invention, U.S. Pat. No. 5,246,015 (Baber) has incorporated a notch into a tube that surrounds and compresses the penile shaft, so that the urethra function is not affected. This notch, however, does not do away with the restricting of blood flow involving other areas of the penis.

SUMMARY OF THE INVENTION

The present invention functions as a simplified erection aid device for human males suffering from impotence problems. A rigid flat disk, has an opening defined by a circular ring, which is fitted around the shaft of a penis. The diameter of the circular ring is approximately 10 percent smaller than the user's penile shaft, when it is fully erected. The penile shaft, when erected, may slightly exceed the circular ring circumference, but should not by more than ¼ of an inch, or 0.65 centimeters. The disk has a rigid extension arm, with the disk and arm being formed as a single piece, or the arm being firmly fixed to the disk.

The penis glans is positioned inside the circular ring, and the disk is moved to the base of the penis, with the extension arm pointing vertically above the disk. The disk is then urged against the pelvic region, using a set of lines, which are attached to a belt that the user wears around his waist.

The lines are fixed to the disk, or pass through holes on the disk, that are approximately 120 degrees from each other, and 120 degrees from the arm, along a line of circumference along the disk. The lines exert a pulling force on the disk, in an opposite direction to an equal pulling force exerted by the extension arm.

The lines are adjustable in length, or position, so that the length of the lines can be tailored to accommodate each user's own particular body size, and distance needed between the belt and the disk, to provide the proper amount of pulling force on the disk. The extension arm is not adjustable, since it is rigid as to length and resists any bending. The end of the extension arm, attaches to the belt, preferably using a Velcro end, that can be fixed to a reciprocating Velcro portion on the belt. The extension arm is shaped so that the disk is positioned vertically at the base of the penis, while it is being worn. The extension arm has a series of bands along its length, or is curved along its length, to account for the greater circumference around the user's belt line than the circumference around a user's groin area.

The line ends have belt loops that the belt passes through, with the lines being adjusted by moving the belt loops closer together, or farther apart from each other along the length of the belt. As the belt loops are moved farther apart, they urge the disk closer to the belt length that is between the belt loops. The result is a direct pulling force that should be in a direction opposite from the penis shaft length.

To use this device, the belt is firmly fastened around the waist, with the belt loops positioned on the belt so that they contact the user's back. At this point in time, the disk and extension arm will be hanging from the lines, resisting against or near the back side of the user's thighs. The disk and extension arm are pulled between the user's legs, and the glans and penile shaft are pushed through the opening defined by the disk's circular ring. The extension arm is attached to the belt length. The lines travel from the belt portion against the user's back, to the disk, with the scrotum being positioned between the lines.

The pressure of the disk, against the pelvic region is created by adjusting the lines as indicated above. As the pull created by the lines is increased, the disk, while maintaining a near vertical position, presses against the pelvic region, causing the veins, which drain blood from the corpus cavernosa region of the penis to compress slightly. When this occurs, the corpus cavernosa regions swell, causing the penis to become erect. The penile shaft circumference, when fully erected, can slightly exceed the opening in the disk. The resulting pressure, placed on the surface of the penile shaft, squeezes the surface veins slightly. This squeezing reduces the surface vein blood flow, to promote continued erection, as would normally be done in a properly functioning user.

Since the disk's pressure against the pelvic region is directly toward the body, rather than directed completely toward the shaft of the penis, flow of fluids in the urethra is unaffected. This allows the user to ejaculate during sexual activity without pain, discomfort, or an appreciable decrease in seminal fluid expelled during ejaculation. Since only certain veins are affected by the pressure of the disk, when worn properly against the pelvic region, the user can maintain an erection for a prolonged period of time, without strangulation of the penis or scrotal area.

Accordingly, it is the object of this invention to provide a penile erection device which allows a male to achieve and sustain an erection when they are suffering from impotence.

It is a further object of this invention to provide a simplified erection aid device whereby a variety of penis sizes can utilize the same device.

It is a further object of this invention to provide a simplified erection aid device that has adjustable features to accommodate users of various body sizes, and to tailor the pressure applied by the device against the pelvic region.

It is a further object of this invention to provide a simplified erection aid device that may be used without interfering with other normal bodily functions such as blood flow to other parts of the penis and scrotum, urination and ejaculation.

It is a further object of this invention to provide a simplified erection aid device that does not physically interfere with the user's ability to engage in sexual activity, and allows exposure of a maximum surface area of the penile shaft for nerve ending stimulation.

DESCRIPTION OF THE DRAWINGS

FIG. 3 is a front right side perspective view of the user's stomach, pelvic region, and upper thighs, with the device properly worn and adjusted.

FIG. 4 is a side cross sectional view of a male's pelvic region, with the device properly worn and adjusted.

FIG. 5 is a cross section of the penile shaft.

FIG. 6 is a side view of the disk and rigid extension arm.

DESCRIPTION OF THE PREFERRED EMBODIMENT

Figure 1:
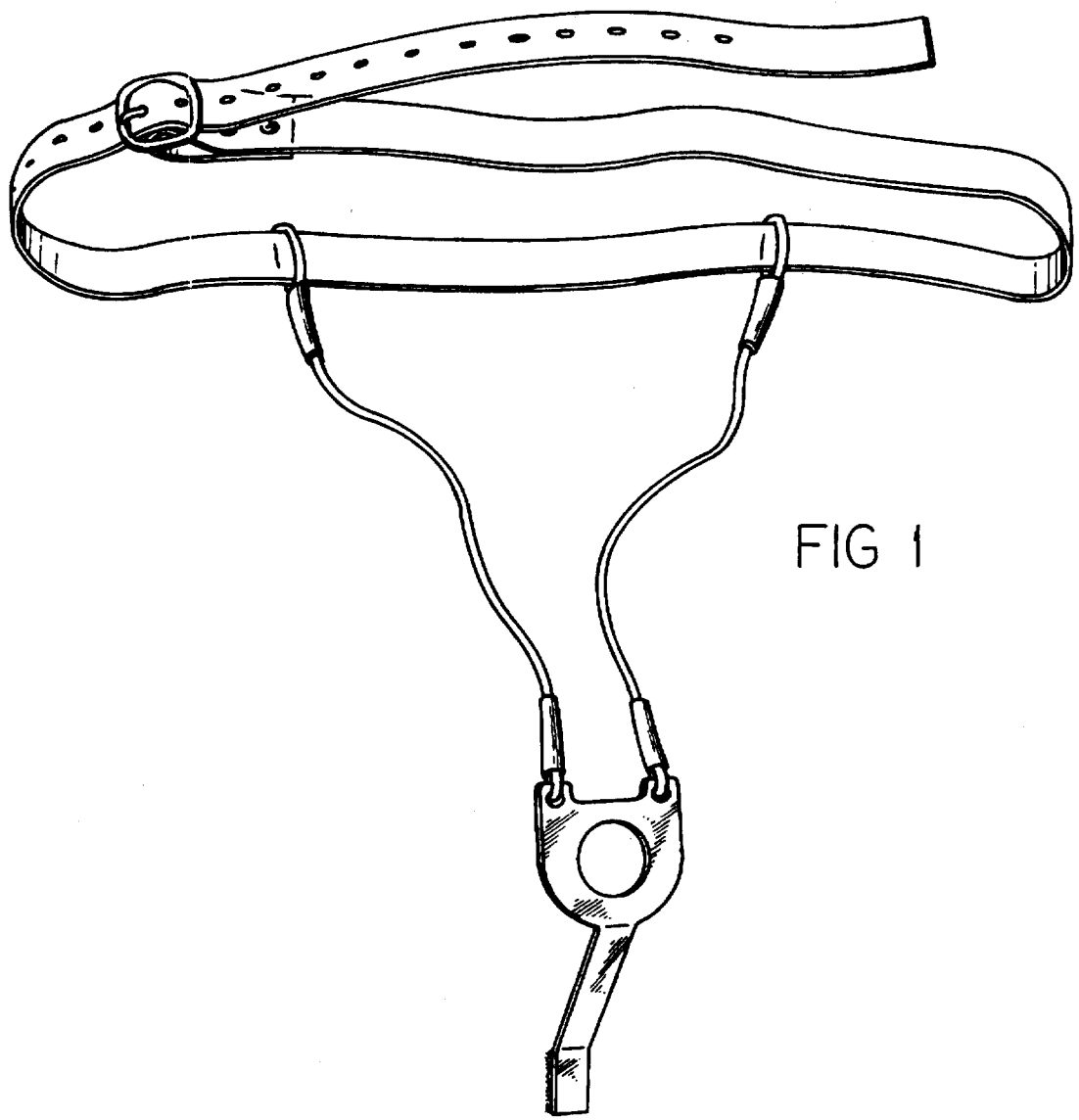
FIG. 1 is a top view of the device, prior to it being worn.

Referring now to FIG. 1, the simplified erection aid device 10 has an annular disk 11 with a circular opening 12 defined by an inner circular ring 13. A set of lines 14 and 15 are secured at one end to the annular disk 11, and secured to a belt 20 at the other end. Although many types of attachment methods can used to secure lines 14 and 15 to the annular disk 11, a simple and effective method is to pass the line 14 through a line hole 16, and pass line 15 through line hole 17, with the ends of each line 14 and 15 forming a loop.

Lines 14 and 15 are secured to the belt 20, preferably by forming the ends of lines 14 and 15 are formed into belt loops 18 and 19. The belt 20, passes through belt loops 18 and 19, which have a loop size that allows the belt loops 18 and 19 to slide along the length of the belt 20 to adjust the tension and pull, between the belt 20 and disk 11.

A rigid extension arm 21 is fixed at a first end to the annular disk 11, with the second end having a means to attach the extension strap 21 to the belt 20. The first end of the extension arm 21 can be permanently fixed to the annular disk 11. The disk 11 and extension arm 21 can also be formed as single piece.

The second end of the extension arm 21 has a means to secure the extension arm 21 to the belt 20. Preferably, the extension arm's 21 second end has a Velcro area 23, that can be secured to a reciprocating Velcro area 23a, along the length of the belt 20.

Figure 2:
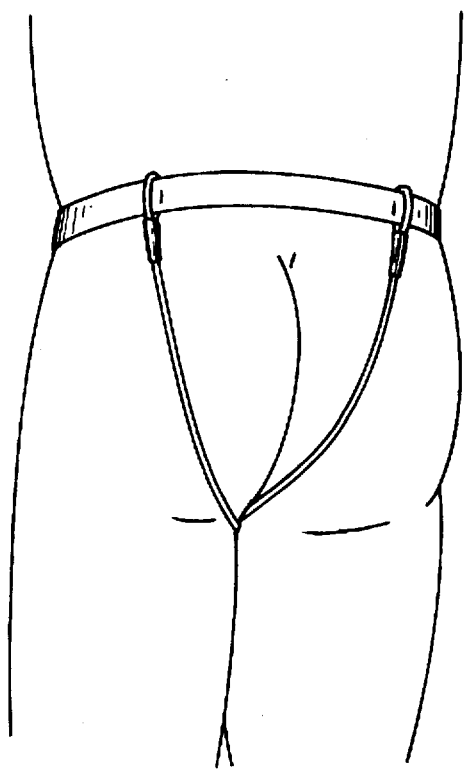
FIG. 2 is a view of the user's back and buttocks, with the device properly worn and adjusted.

Referring also to FIGS. 2 and 3, line hole 16, and line hole 17 are located on the annular disk 11, and are spaced apart so that the scrotum 43 may be placed between lines 14 and 15, when the simplified erection aid device 10 is worn. The two adjustable lines 14 and 15 provide a pulling force to the bottom of the annular disk 11 against a user's pelvic area and scrotum 43, with the lines 14 and 15 secured to the annular disk 11 and spaced apart so that the user's scrotum 43 may be placed between said two lines 14 and 15. Said lines 14 and 15 are attached to the annular disk 11, with the attachment points being below the circular opening,. and the penile shaft 44 when the device is worn with the user's penile shaft 44 being inserted through the annular disk 11. The scrotum 43 is positioned between the lines 14 and 15 as they run from the annular disk 11, between the user's legs 41 and 41a, and over the user's buttocks, where they are secured at their other ends to a belt 20 that is adapted to be worn about the waist of the user. The point at which the extension arm's 21 first end is fixed or formed to the annular disk with the line hole 16, and line hole 17, are all equidistant from each other, or each separated by 120 degrees along a line of circumference.

The simplified erection aid device 10 is put on the user by attaching the belt 20 around the user's waist, with the belt loops 18 and 19 positioned along the belt's 20 length, so that they contact the user's lower back 31. The simplified erection aid device 10 will initially hang directly downwards from the user's back 31, until the user pulls the disk 11 and extension arm 21 between their legs to the front side of the user. The glans 52 and penile shaft 44 are pushed through the circular opening 12, and the annular disk 11 is moved along the penile shaft 44 until the disk 11 encounters the pelvic region at the base of the penile shaft 44. Line 14 is positioned between the scrotum 43 and right thigh 41. Line 15 is positioned between the scrotum 43 and the right thigh 41a, with both lines contacting their respective right or left buttock.

The circular opening 12 should accommodate the circumference of the penile shaft 44, when it is fully erected, at the point where the penile shaft 44 connects to the pelvic region. The size of the annular disk 10 and circular opening 12 are important to correct operation of the simplified erection aid device. Generally, the diameter of the opening 12 should be 7 to 12 percent less than an erect penile shaft 44. For users with an average size erect penile shaft 44, that has a diameter up to a maximum of 1.50 inches, or a circumference of 4.50 inches, the inner circular ring 13 should define a circular opening 12, with a diameter of 1⅜ inches. If the penile shaft 44 exceeds these average measurements, when fully erected, a larger circular opening 12 is necessary, so that the penile shaft 44 is not constricted beyond safe and comfortable limits. Typically, the circular opening 12 should have a circumference that is equal to 90 percent of the erected penile shaft circumference.

Once the annular disk 11 is positioned on the penile shaft 44, the extension arm 21 is pulled upward, and secured to the belt 20. The extension arm 21 is secured to the belt 20, preferably using a Velcro area 23 on the second end of the extension strap 21, which attaches to a reciprocating Velcro portion 23a on the belt 20.

Referring also to FIGS. 4 and 5, the disk 11 must be pressed firmly against the pelvic region 56, so that the annular disk 11 surrounds the base of the penile shaft 44, and presses against the pelvic region 56 and a portion of the scrotum 43. The extension arm 21 positions the annular disk 11 vertically against user's body. Lines 14 and 15 are adjusted to provide the necessary pulling force on the annular disk 11, so as to press the annular disk 11 against the user's pelvic area 56 and scrotum 43.

The extension arm 21 is rigidly formed so that the disk 11 is held vertically against the base of the penis. This is necessary to properly affect the soft tissue area's of the user's body, when the lines 14 and 15 apply a pulling force to the disk 11.

The length of the extension arm 21 is preferably shaped with curves or bends, so that the disk 11 is offset vertically along line 72, which extends horizontal to line 71 that intersects the belt 20 at the point where the extension arm 21 attached. In this manner, the disk 11 is positioned firmly and vertically against the base of the penis, even though the typical user has a greater body circumference around their stomach line than around their hip and groin area.

When lines 14 and 15 pull on the disk, the force is substantially limited to a horizontal backwards force, in relation to the user, applied to the bottom of the disk 11, which in turn applies pressure to the soft tissue and underlying blood vessels near the bottom side of the base of the penile shaft 44.

The user adjusts lines 14 and 15 to provide less pulling force on the disk 11, by moving belt loop 18 and 19 toward each other. The user increases the pulling force on the annular disk by moving belt loop 18 and 19 away from each other, along the length of the belt 20.

When the annular disk 11 is pressed against the pelvic area 56, pressure is applied to the veins that drain the corpus cavernosa 51, which extends several inches into the pelvic area 56 from the penile shaft 44. The pressure applied from the disk 11 slightly deforms or flattens the veins that drain blood from the corpus cavernosa 51 by reducing the flow rate of blood through the veins.

When the flow rate through the arteries, that deliver blood to the corpus cavernosa 51 exceeds the amount that is drained through the veins, the corpus cavernosa 51 swells and stiffens the penile shaft 44 into an erection. The inner circular ring 13 that surrounds the penile shaft 44 must have a circumference that assists in maintaining the erection, without affecting other bodily functions, such as urination or ejaculation. Preferably, the circumference of the timer circular ring 13 should be only slightly smaller than the circumference of the penile shaft 44 when it is fully erected. This will cause the draining veins to flatten slightly, decreasing the amount of blood they can drain from the corpus cavernosa 51. This slight flattening of the surface veins is a normal effect of erection in properly functioning males.

The user, while wearing the simplified erection aid device 10, can urinate or ejaculate without any impedance to the discharge of fluid through the urethra 53, since the inner circular ring 13 applies a slight constricting pressure to the surface area and veins under the surface only, and does not strangle the penile shaft 44 to affect the flow of fluids within the corpus cavernosa 51 or urethra 53.

From the foregoing statements, summary and description in accordance with the present invention, it is understood that the same are not limited thereto, but are susceptible to various changes and modifications as known to those skilled in the art and we therefore do not wish to be limited to the details shown and described herein, but intend to cover all such changes and modifications which would be encompassed by the scope of the appended claims.

I claim:

1. An erection aid device comprising:

(a) a belt adapted to be worn about the waist of a user, (b) an annular disk having an inner circular ring that defines a circular opening adapted to receive a shaft of a penis, said annular disk adapted for applying pressure to the pelvic area of the user, (c) two adjustable lines connected to a bottom portion of the annular disk below said circular opening and adjustably connected to said belt, said lines adapted to extend around the user's scrotum, between the user's legs, and over the buttocks of the user, said lines providing a pulling force to the bottom portion of the annular disk causing the pressure applied to the pelvic area, (d) a rigid extension arm, having first and second ends, said first end connected to said annular disk, said second end including means for attaching the extension arm to said belt, in which the extension arm is shaped so that the disk is positioned vertically along a plane from 1 inch to 1.50 inches from a vertical line that intersects the belt at the point where the extension arm is attached to the belt.

2. An erection aid device, as described in claim one, in which the annular disk and extension arm are formed as a single piece.

3. An erection aid device, as described in claim one, in which the point on the annular disk which the extension arm's first end is fixed or formed to the annular disk with the line holes are being equidistant from each other, or each separated by 120 degrees along a line of circumference.

* * * * *